United States Patent [19]

Fechter et al.

[11] Patent Number: 5,684,190
[45] Date of Patent: Nov. 4, 1997

US005684190A

[54] RECOVERY OF AMINO ACID

[75] Inventors: Wolfgang Ludwig Fechter, Westville; Jonathan Hugh Dienst, Sandton; John Frank Le Patourel, Midrand, all of South Africa

[73] Assignee: AECI Limited, Johannesburg, South Africa

[21] Appl. No.: 640,909

[22] PCT Filed: Nov. 18, 1994

[86] PCT No.: PCT/GB94/02544

§ 371 Date: May 9, 1996

§ 102(e) Date: May 9, 1996

[87] PCT Pub. No.: WO95/14002

PCT Pub. Date: May 26, 1995

[30] Foreign Application Priority Data

Nov. 19, 1993 [ZA] South Africa ............... 938660

[51] Int. Cl.$^6$ .................................................. C07C 227/38
[52] U.S. Cl. .................................................... 562/554
[58] Field of Search ........................................ 562/554

[56] References Cited

U.S. PATENT DOCUMENTS 2,894,026  7/1959  Hause .................................. 562/554
4,691,054  9/1987  Tosa .................................... 562/554
4,714,767  12/1987  Tanaka .................................. 562/554

*Primary Examiner*—Michael L. Shippen
*Attorney, Agent, or Firm*—Greenlee, Winner and Sullivan, P.C.

[57] ABSTRACT

A method of recovering a desired amino acid such as L-lysine from an aqueous solution containing the desired amino acid and impurities, includes the steps of passing the solution over a primary cation exchange resin to adsorb the desired amino acid onto the resin at a pH lower than the isoelectric point of the desired amino acid, eluting the desired amino acid from the resin using a suitable eluent having a pH higher than the isoelectric point of the desired amino acid to produce a first solution, passing the first solution over a secondary cation exchange resin to adsorb one or more of the impurities and to produce a second solution leaving the resin, collecting the second solution until the ratio of the concentrations of a selected impurity to the desired amino acid reaches a chosen value to produce a third solution which contains a lower level of impurities than the first solution, and recovering the desired amino acid from the third solution. This method avoids the need for a costly crystallization step to produce a final product.

12 Claims, 3 Drawing Sheets

5,684,190

RECOVERY OF AMINO ACID

BACKGROUND OF THE INVENTION

This invention relates to a method of recovering an amino acid such as L-lysine from a solution containing the amino acid and various impurities including potassium and magnesium ions, other cations, ammonia and other amino acids.

The amino acid L-lysine is normally produced by large-scale fermentation that results in an impure L-lysine-containing solution, known as "broth", at a concentration of between 80 and 110 g/l. L-lysine is generally produced in a stable and non-hygroscopic hydrochlorinated form, which has the chemical formula $H_2N(CH_2)_4CHNH_2CO_2H.HCl$. So-called "feed-grade" lysine is usually of a purity of not less than 98.5% by mass L-lysine.HCl with a moisture content of not more than 1% by mass.

The conventional L-lysine purification route begins with the fermentation broth which is passed over a cation exchange resin, either before or after biomass removal by filtration or centrifuging. The L-lysine is adsorbed onto the resin at a low pH and is then stripped from the resin at a high pH using an eluent such as ammonium hydroxide. The eluent containing L-lysine and ammonia, with impurities such as potassium and magnesium ions and other amino acids, is then concentrated by evaporation. At the same time the bulk of the ammonia is stripped from the solution. The solution is then acidified with hydrochloric acid, after which the L-lysine is crystallized as $L$-lysine.$HCl.2H_2O$, either by means of a batch cooling crystallizer or an evaporative crystallizer, in a process termed "crystallisation". The wet crystals of L-lysine are separated from the mother liquor using a centrifuge or filter and then dried, typically by means of a fluid bed drier. The mother liquor may be recycled and at least a portion needs to be purged as a waste stream, resulting in the loss of some lysine.

There is a need for an improved method for the recovery of amino acids such as L-lysine.

SUMMARY OF THE INVENTION

According to a first aspect of the invention there is provided a method of recovering a desired amino acid from an aqueous solution containing the desired amino acid and impurities, which method includes the steps of:

(i) passing the aqueous solution over a primary cation exchange resin to adsorb the desired amino acid onto the resin at a pH lower than the isoelectric point of the desired amino acid;

(ii) eluting the desired amino acid from the resin using a suitable eluent having a pH higher than the isoelectric point of the desired amino acid to produce a first solution;

(iii) passing the first solution over a secondary cation exchange resin to adsorb one or more of the impurities and to produce a second solution leaving the resin;

(iv) collecting the second solution until the ratio of the concentrations of a selected impurity to the desired amino acid reaches a chosen value to produce a third solution which contains a lower level of impurities than the first solution; and (v) recovering the desired amino acid from the third solution.

The amino acid to be recovered may be any amino acid which is sufficiently water soluble, for example lysine, glycine, threonine, proline, arginine and methionine.

The preferred amino acid is L-lysine, in which case there is provided a method of recovering L-lysine from an aqueous solution containing the L-lysine and impurities, which method includes the steps of:

(i) passing the aqueous solution over a primary cation exchange resin to adsorb the L-lysine onto a resin at a pH of between 1.5 and 4 inclusive;

(ii) eluting the L-lysine from the resin using a suitable eluent having a pH higher than 9.59 to produce a first solution;

(iii) passing the first solution over a secondary cation exchange resin to adsorb one or more of the impurities and to produce a second solution leaving the resin;

(iv) collecting the second solution until the ratio of the concentrations of a selected impurity to L-lysine reaches a chosen value to produce a third solution which contains a lower level of impurities than the first solution; and (v) recovering the L-lysine from the third solution.

According to a second aspect of the invention there is provided a method for the recovery of a desired amino acid from a first solution produced by passing an aqueous solution containing the desired amino acid over a primary cation exchange resin to adsorb the desired amino acid onto the resin, and then eluting the desired amino acid from the resin using a suitable eluent having a pH higher than the isoelectric point of the desired amino acid, the first solution containing in addition impurities including for example potassium, calcium, sodium and magnesium ions and possibly other amino acids, which method includes the steps of:

(iii) passing the first solution over a secondary cation exchange resin to adsorb one or more of the impurities and to product a second solution leaving the resin;

(iv) collecting the second solution until the ratio of the concentrations of a selected impurity to the desired amino acid reaches a chosen value to produce a third solution which contains a lower level of impurities than the first solution; and (v) recovering the desired amino acid from the third solution.

Again, the preferred amino acid for recovery is L-lysine in which case there is provided a method for the recovery of L-lysine from a first solution produced by passing an aqueous L-lysine containing solution over a primary cation exchange resin to adsorb the L-lysine onto the resin, and then eluting the L-lysine from the resin using a suitable eluent having a pH higher than 9.59, the first solution containing in addition impurities including potassium, calcium, sodium and magnesium ions and other amino acids, which method includes the steps of:

(iii) passing the first solution over a secondary cation exchange resin to adsorb one or more of the impurities and to produce a second solution leaving the resin;

(iv) collecting the second solution until the ratio of the concentrations of a selected impurity to L-lysine reaches a chosen value to produce a third solution which contains a lower level of impurities than the first solution; and (v) recovering the L-lysine from fie third solution.

The aqueous solution used in step (i) may be treated prior to step (i) to remove biomass by filtration or centrifuging.

Preferably, the first solution is not processed in any way between step (ii) and step (iii).

In step (ii) the suitable eluent is preferably ammonium hydroxide.

In step (iv), the second solution may be collected from before, at or after the breakthrough of the desired amino acid. In step (iv) generally a small amount of the desired amino acid is adsorbed onto the resin until the desired amino acid breaks through. However, the impurities continue to be adsorbed for a further period of time. The second solution may be collected until before, at or after the breakthrough of the selected impurity.

Clearly the chosen value for the ratio of the concentrations of the selected impurity to the desired amino acid will be one where the concentration of the selected impurity is very low and the concentration of the desired amino acid is high.

The second solution is preferably collected from before the breakthrough of the desired amino acid until just after the breakthrough of the selected impurity, i.e. when the ratio of the concentrations of the selected impurity to the desired amino acid is close to 0:1.

The secondary cation exchange resin is preferably located in a bed which may be operated as a fixed bed or as a countercurrent rotating fixed bed or as a countercurrent moving bed.

In step (iv), when the desired amino acid is L-lysine, the selected impurity may be potassium, but the selected impurity, usually the impurity which breaks through first in sufficient quantifies to affect the quality of the end product, may be any one or more of the other impurities present.

In step (v), the third solution may be concentrated and any ammonia from the ammonium hydroxide eluent stripped off, preferably using multiple effect evaporators, optionally acidified with a suitable acid such as hydrochloric acid, and then dried in a suitable drying apparatus to provide the purified amino acid, e.g. L-lysine either as L-lysine or as L-lysine.HCl.

DESCRIPTION OF EMBODIMENTS

The crux of the invention is that a method for the recovery of a desired amino acid includes the use of a secondary cation exchange resin after the use of a primary cation exchange resin, to produce a purified amino acid solution which does not require a costly crystallisation step to produce a final product.

The method of the invention is conventional in so far as the first two steps are concerned, viz the use of the primary ion exchange resin and the elution of the first solution therefrom.

Thereafter, in step (iii) of the method of the invention, the first solution is passed over a secondary cation exchange resin to adsorb one or more of the impurities and to produce a second solution leaving the resin. Preferably, there is no intermediate processing between step (ii) and step (iii).

The secondary cation exchange resin may be provided in a bed which may be operated as a fixed bed or as a countercurrent rotating fixed bed or as a countercurrent moving bed. In both cases, the behaviour on the bed is such that a small amount of desired amino acid adsorbs, in spite of the high pH of the first solution, until the desired amino acid breaks through.

Figure 2:
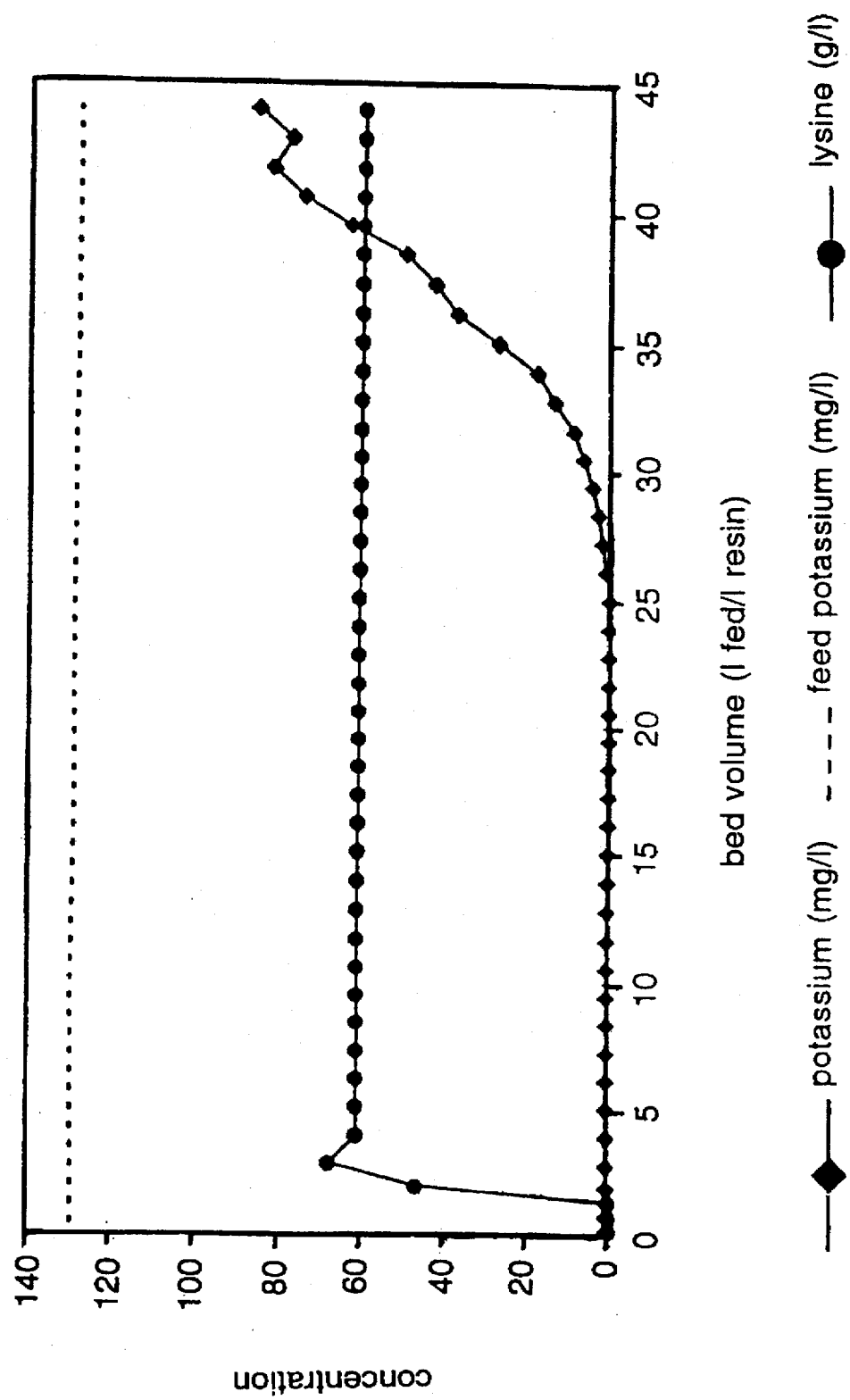
FIG. 2 and FIG. 3 are typical second solution concentration profiles from the operation of the method of the invention. The lysine concentration expressed as g/l and the potassium concentration expressed as mg/l are plotted against the number of bed volumes fed. The potassium concentration in the first solution in mg/l is also plotted for comparison.
Figure 3:
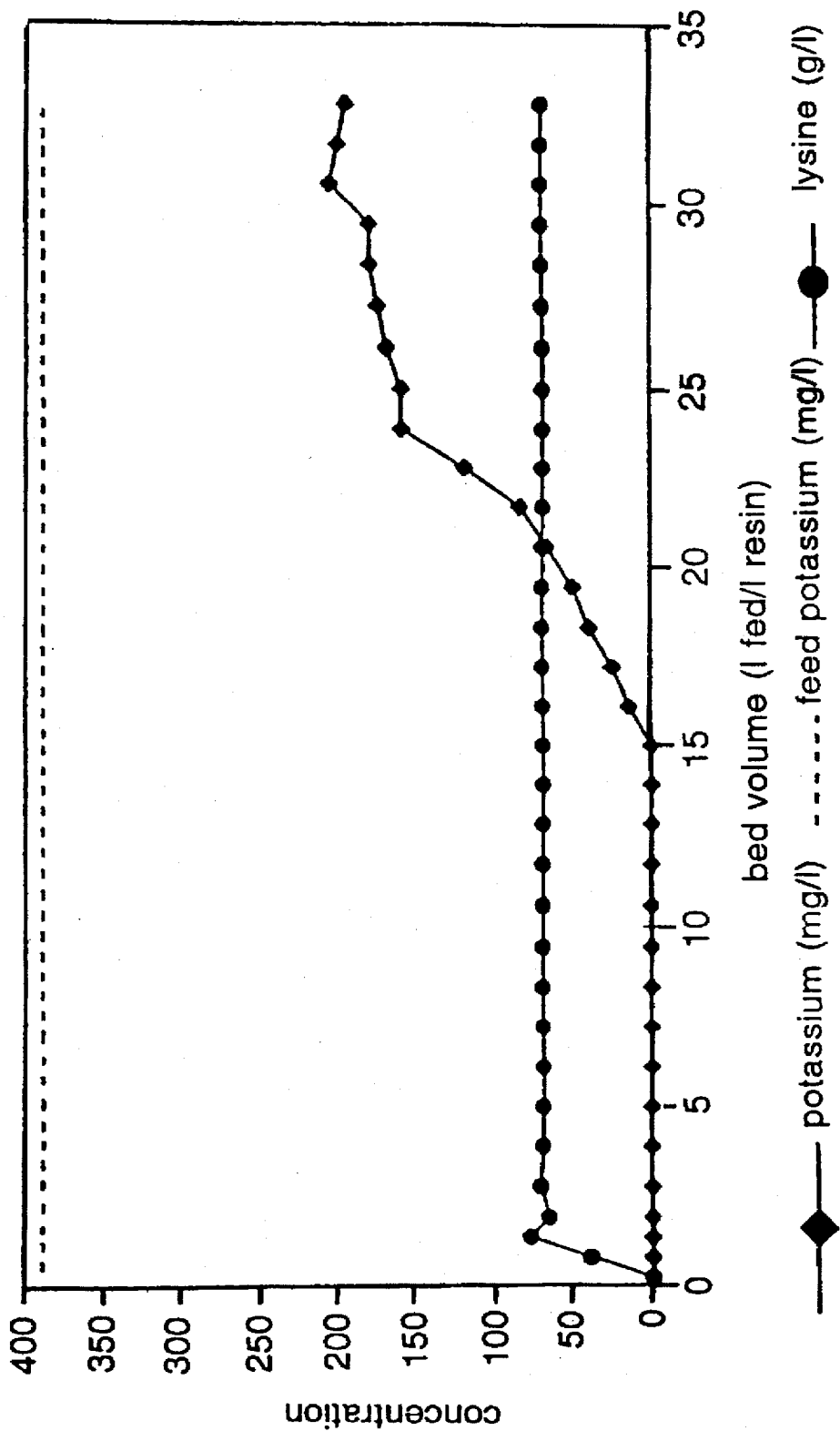

As is illustrated in FIG. 2 and FIG. 3 for L-lysine the L-lysine breaks through and reaches the second solution after the equivalent of a few bed volumes of the first solution have been passed through the bed. The potassium, which in the case of these experiments is the major contaminant to be removed by the secondary ion exchange step, continues to be adsorbed for some time, typically until 10 to 35 bed volumes of the first solution have been passed through the bed. In approximately the time between L-lysine and potassium breakthrough, the second solution is collected at the outlet of the secondary cation exchange resin bed to form a third solution which contains L-lysine and apart from ammonium is substantially cation free.

Suitable primary and secondary cation exchange resins include the strong acid cation exchange resins such as DOWEX XUS 43518 and XUS 40406 and DOWEX C500ES. DOWEX is a registered trade mark of The Dow Chemical Company. The strong acid cation resins are typically sulphonated copolymers of styrene and divinyl benzene. Both get and macroporous resins are suitable. These resins typically have a resin capacity of the order of 1,9 equivalents/liter but resins with much lower or higher capacities are also suitable.

Figure 1:
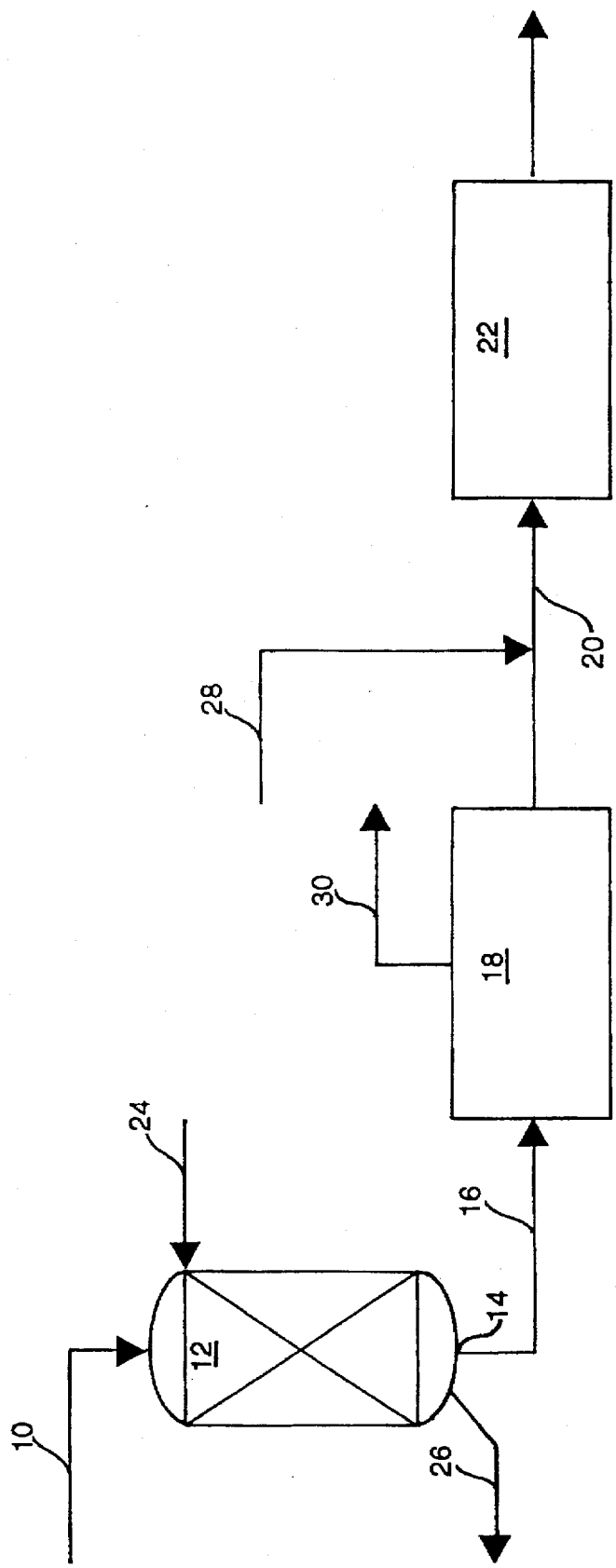
FIG. 1 is a schematic flow sheet for a method of L-lysine recovery according to the invention.

This method is illustrated for L-lysine in FIG. 1 where the first solution, being the primary ion exchange step eluent, is fed via a line 10 to a secondary ion exchange column 12. The second solution leaves the secondary ion exchange column 12 at 14. At this point the third solution is collected and is passed via a line 16 to an evaporator 18 where ammonia (from the eluent) is removed via a line 30 and a high purity lysine solution is produced in line 20. This stream can be sold as the product or passed to a lysine drier 22. Various acids, for example hydrochloric acid may be added into the line 20 via a line 28 if desired.

When the ratio of the concentrations of the selected impurity to L-lysine has reached the chosen value, the secondary cation exchange resin bed in the column 12 needs to be regenerated using an acid such as hydrochloric acid or sulphuric acid which may be fed into the column 12 via a line 24. Thereafter, the bed in the column 12 is washed with demineralized or potable water, after which it is ready for re-use. The spent regenerant is bled out of the column 12 via a line 26, and may be recycled to recover the small quantity of L-lysine therein, or may be discarded. This recycling leads to higher recoveries of L-lysine.

The third solution leaving the column 12 may be concentrated using multiple effect evaporators, which also remove any ammonia from the ammonium hydroxide eluent, yielding a high purity lysine solution.

Acidification with hydrochloric acid and subsequent drying in a suitable drying apparatus will produce feed grade lysine, i.e. 98.5% by mass L-lysine.HCl with a moisture content of not more than 1% by mass. Any cations remaining in the lysine liquor at the hydrochlorination operation will be converted into chloride salts and will then be present as an ash impurity in the product. The fact that drying, rather than crystallization is employed for the final solid liquid separation provides an additional advantage, namely flexibility as far as the final form of the product is concerned. Thus the final product may be a powder produced in a spray drier, a coarse powder or a fine granular product produced in a fluid bed drier, flakes produced in a drum drier or intermediate to coarse granules produced in a granulator drier.

Although the method is illustrated for L-lysine, the method is also applicable to other water soluble amino acids such as glycine, threonine, proline, arginine and methionine.

The isoelectric points of these amino acids are as follows:

| | |
|---|---|
| Lysine | 9.59 |
| Glycine | 5.97 |
| Threonine | 5.64 |
| Proline | 6.3 |
| Arginine | 11.15 |
| Methionine | 5.74 |

Details of experimental work carried out in relation to the method of the invention will now be given.

Experimental Work

For most of the experimental work, the only impurity measured was potassium (as K+) as it was found to make up approximately 80% of the non-ammonium cationic impurities in the L-lysine liquor after the primary ion-exchange operation. Where other cationic impurities were measured they confirmed that the potassium concentration was a reasonable indicator of the total impurities. The experiments were performed on a fixed bed ion-exchange column of 25 mm diameter with bed heights varying between 200 mm and 900 mm. The process consisted of the following steps:

1. Adsorption. The eluent (first solution) from the primary ion-exchange operation was fed onto the secondary ion-exchange resin bed at a range of velocities from 12 to 30 m/h. The L-lysine and potassium concentrations were monitored and feed continued until the desired ratio of potassium to L-lysine was reached.
2. Drain. The column was then drained. The drained liquor may be added to the product stream.
3. Regeneration. The column was regenerated with sulphuric or hydrochloric acid at typical concentrations of between 5 and 10%.
4. Wash. The column was then washed with several bed volumes of demineralised water.

TABLE 1 shows the results of the various runs.

| Run number | | 8 | 12 | | 14 | |
|---|---|---|---|---|---|---|
| feed K+ | mg/l | 259 | 230 | | 388 | |
| feed lysine | g/l | 42.5 | 50.1 | | 68.7 | |
| feed K+:lysine ratio | mg/kg | 6090 | 4590 | | 5650 | |
| product impurity | as % KCl | 0.1 | 0.05 | 0.01 | 0.05 | 0.1 |
| K+ adsorbed | mg/l resin | 10.1 | 8.01 | 6.51 | 7.31 | 7.86 |
| K+ removed | % of feed | 91 | 95 | 99 | 95 | 90 |
| lysine loss on resin | % of feed | 5.3 | 7.6 | 4 | 4 | 3 |
| resin volume | ml | 250 | 100 | | 450 | |
| resin height | cm | 49 | 20 | | 89 | |
| resin used | | | DOWEX C500 ES | | | |

| Run number | | 16 | 17 | 22 |
|---|---|---|---|---|
| feed K+ | mg/l | 192 | 129 | 322 |
| feed lysine | g/l | 92 | 61 | 78.8 |
| feed K+:lysine ratio | mg/kg | 2090 | 2110 | 4090 |
| product impurity | as % KCl | 0.01 | 0.01 | 0.05 |
| K+ adsorbed | mg/l resin | 5.2 | 4.35 | 5.74 |
| K+ removed | % of feed | 97 | 98 | 94 |
| lysine loss on resin | % of feed | 2 | 4.7 | 10 |
| resin volume | ml | 450 | 450 | 275 |
| resin height | cm | 89 | 89 | 54 |
| resin used | | | DOWEX XUS 4046 | |

TABLE 2 shows cation results from a typical secondary ion exchange experiment.

| Run number 14 | | K | Ca | Fe |
|---|---|---|---|---|
| feed cation | mg/l | 388 | 6.3 | 2.8 |
| feed lysine | g/l | 68.7 | 68.7 | 68.7 |
| feed ratio | mg/kg | 5650 | 90 | 40 |
| removal at 0.1% KCl impurity | as % feed | 90 | 83.9 | 9.8 |
| ration relative to lysine at 0.1% KCl impurity | mg/kg | 566 | 14.9 | 37 |

| Run number 14 | | Mg | Na |
|---|---|---|---|
| feed cation | mg/l | 55.3 | 28.4 |
| feed lysine | g/l | 68.7 | 68.7 |
| feed ratio | mg/kg | 800 | 410 |
| removal at 0.1% KCl impurity | as % feed | 99.8 | 47.8 |
| ratio relative to lysine at 0.1% KCl impurity | mg/kg | 1.7 | 217 |

The results of Run Numbers 14 and 17 are illustrated in FIG. 2 and FIG. 3.

The method of the invention has the advantage that it is capable of removing impurities that are not separated from the L-lysine in the primary (conventional) ion exchange resin step in a secondary ion exchange resin step. In this step, the impurity levels can be reduced to a level that is low enough to eliminate the need for further purification by crystallisation, resulting in capital and operating cost reductions.

The method of the invention produces a high purity L-lysine solution which provides for flexibility with respect to the product form. Further, the method of the invention results in higher recoveries of feed grade lysine from aqueous solutions than the conventional process which utilises crystallisation.

We claim:

1. A method of recovering a desired amino acid from an aqueous solution containing the desired amino acid and impurities, which method includes the steps of:
   (i) passing the aqueous solution over a primary cation exchange resin to absorb the desired amino acid onto the resin at a pH lower than the isoelectric point of the desired amino acid;
   (ii) eluting the desired amino acid from the resin using a suitable eluent having a pH higher than the isoelectric point of the desired amino acid to produce a first solution;
   (iii) passing the first solution over a secondary cation exchange resin to absorb one or more of the impurities and to produce a second solution leaving the resin;
   (iv) collecting the second solution until the ratio of the concentrations of a selected impurity to the desired amino acid reaches a chosen value to produce a third solution which contains a lower level of impurities than the first solution; and
   (v) recovering the desired amino acid from the third solution.

2. A method according to claim 1 wherein the first solution is not processed in any way between step (ii) and (iii).

3. A method according to claim 1 wherein in step (ii) the suitable eluent is ammonium hydroxide.

4. A method according to claim 1 wherein the primary cation exchange resin and the secondary cation exchange resin are strong acid cation exchange resins.

5. A method according to claim 1 wherein in step (iv) the second solution is collected from before the breakthrough of the desired amino acid until just after the breakthrough of the selected impurity.

6. A method of recovering L-lysine from an aqueous solution containing the L-lysine and impurities, which method includes the steps of:

(i) passing the aqueous solution over a primary cation exchange resin to absorb the L-lysine onto the resin at a pH of between 1.5 and 4 inclusive;

(ii) eluting the L-lysine from the resin using a suitable eluent having a pH higher than 9.59 to produce a first solution;

(iii) passing the first solution over a secondary cation exchange resin to absorb one or more of the impurities and to produce a second solution leaving the resin;

(iv) collecting the second solution until the ratio of the concentrations of a selected impurity to L-lysine reaches a chosen value to produce a third solution which contains a lower level of impurities than the first solution; and (v) recovering the L-lysine from the third solution.

7. A method according to claim 6 wherein the first solution is not processed in any way between step (ii) and step (iii).

8. A method according to claim 6 wherein in step (ii) the suitable eluent is ammonium hydroxide.

9. A method according to claim 6 wherein the primary cation exchange resin and the secondary cation exchange resin are strong acid cation exchange resins.

10. A method according to claim 6 wherein in step (iv) the second solution is collected from before the breakthrough of the L-lysine until just after the breakthrough of the selected impurity.

11. A method according to claim 6 wherein in step (iv) the selected impurity is potassium.

12. A method according to claim 6 wherein in step (v), the third solution is concentrated and any ammonia is stripped off, and the third solution is optionally acidified with hydrochloric acid, and dried to provide purified L-lysine either as L-lysine or as L-lysine HCl.

* * * * *

UNITED STATES PATENT AND TRADEMARK OFFICE
CERTIFICATE OF CORRECTION

PATENT NO. : 5,684,190

DATED : November 4, 1997

INVENTOR(S) : Fechter et al.

It is certified that error appears in the above-identified patent and that said Letters Patent is hereby corrected as shown below:

In column 2, line 32, delete "product" and replace with --produce--.

In column 2, line 59, delete "fie" and replace with --the--.

In column 4, line 20, delete "get" and replace with --gel--.

In column 5, Table 1, delete "the various runs" and replace with --various runs--.

In column 5, Table 1, last line, delete "4046" and replace with --40406--.

Signed and Sealed this

Twentieth Day of January, 1998

BRUCE LEHMAN

Attest:

Attesting Officer

Commissioner of Patents and Trademarks